(12) United States Patent
Evans et al.

(10) Patent No.: US 10,755,803 B2
(45) Date of Patent: Aug. 25, 2020

(54) ELECTRONIC HEALTH RECORD SYSTEM CONTEXT API

(71) Applicant: Allscripts Software, LLC, Raleigh, NC (US)

(72) Inventors: Thomas William Evans, Concord, CA (US); Jonathan Mark Malek, Sacramento, CA (US); Matthew Christopher Douglass, San Francisco, CA (US); Ryan Paul Howard, San Francisco, CA (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 0 days.

(21) Appl. No.: 14/318,500

(22) Filed: Jun. 27, 2014

(65) Prior Publication Data
US 2015/0379205 A1 Dec. 31, 2015

(51) Int. Cl.
*G06Q 30/02* (2012.01)
*G06F 17/27* (2006.01)
*G16H 10/60* (2018.01)
*G06F 19/00* (2018.01)

(52) U.S. Cl.
CPC ............. *G16H 10/60* (2018.01); *G06F 19/00* (2013.01)

(58) Field of Classification Search
CPC ........ G06Q 50/22; G06Q 50/24; G06Q 40/08; G06Q 10/10; G06Q 20/20; G06F 19/322; G06F 19/00; G16H 80/00
See application file for complete search history.

(56) References Cited

U.S. PATENT DOCUMENTS

| | | | | |
|---|---|---|---|---|
| 5,664,109 | A | * | 9/1997 | Johnson ................ G06F 19/322 705/2 |
| 2009/0157432 | A1 | * | 6/2009 | Palmroos et al. ................ 705/3 |
| 2010/0131292 | A1 | * | 5/2010 | Hawkins et al. ................ 705/3 |
| 2011/0289497 | A1 | * | 11/2011 | Kiaie et al. .................... 717/171 |
| 2012/0110360 | A1 | * | 5/2012 | Lin et al. ....................... 713/324 |
| 2012/0232926 | A1 | * | 9/2012 | Boyle .................. G06F 19/327 705/3 |

* cited by examiner

*Primary Examiner* — Maroun P Kanaan
(74) *Attorney, Agent, or Firm* — Medley, Beherns & Lewis, LLC

(57) ABSTRACT

Embodiments allow for the retrieval of information identifying the current context (patient being seen, medical record associated with the patient, or medical field selected) of a practice member. That information may be used as a key for subsequent API calls to match data submitted with records in an EHR system. In addition, a confidence level may be associated with that context. The confidence level may describe the level of confidence that context is correctly associated with that key.

16 Claims, 8 Drawing Sheets

FIG. 7 practice fusion™

Home | Schedule | Charts | eRx | Messages | Labs | Documents(1) | Reports | Setup Patients | Unsigned Charts | Maria TestAdult × | Jessica TestChild × | Karen TestToddler ×

Chart
Basic
Insurance
Settings

Maria TestAdult
Female, 47 yrs
DOB: 12/10/1964

Patient Actions ▽

[+] Start a chart note

Summary
PMH
Dx History
Rx List
Allergies
Adv Directives
Immunizations
Growth
Lifestyle Facesheet | Activity | Appointments | Referrals | eScripts | Messages | Documents | Access History Diagnoses Hypertension, benign (401.1)
Hyperlipidemia, mixed (272.2)
Diabetes II, uncomplicated (250.00)

Prescriptions

Lisinopril 10mg tablet

Events
☐ 04/13/2012
☐ 09/10/2011
☐ 08/06/2010

Drug Allergies

No known drug allergies

PMH

Sulfa drugs (rash)

Diabetes, hypertension both parents had MIs in their 40s employed in sales, on the road frequently

ELECTRONIC HEALTH RECORD SYSTEM CONTEXT API

BACKGROUND

Field

This field is generally related to interfacing with electronic health record systems.

Background

Electronic Health Records

Medical records related to a patient's health information are essential to the practice of medical care. Traditionally, medical records were paper-based documents. The emergence of electronic medical records (EMR), which are digital version of the paper chart that contains all of a patient's medical history from one medical practice, offers medical professionals and patients with new functionalities and efficiencies that paper-based medical records cannot provide. An electronic health record (EHR), also known as an electronic medical record (EMR), is a collection of electronically stored information about an individual patient's medical history. EHRs may contain a broad range of data, including demographics, medical history, medication history, allergies, immunization records, laboratory test results, radiology images, vital signs, personal statistics like age and weight, and billing information. Many commercial EHR systems combine data from a number of health care services and providers, such as clinical care facilities, laboratories, radiology centers, and pharmacies.

EHRs are a drastic improvement over paper-based medical records. Paper-based medical records require a large amount of physical storage space. Paper records are often stored in different locations, and different medical professionals may each have different and incomplete records about the same patient. Obtaining paper records from multiple locations for review by a health care provider can be time consuming, complicated, and sometimes impossible. In contrast, EHR data is stored in digital format, and thus are more secure and can be accessed from anywhere. EHR systems significantly simplify the reviewing process for health care providers. Because records in EHRs can be linked together, EHRs vastly improve the accessibility of health records and the coordination of medical care.

EHRs also decrease the risk of misreading errors by health care professionals. Poor legibility is often associated with handwritten, paper medical records, which can lead to medical errors. EHRs, on the other hand, are inherently legible given that they are typically stored in typeface. In addition, electronic medical records enhance the standardization of forms, terminology and abbreviations, and data input, which help ensure reliability of medical records, and standardization of codesets and storage of EHR data means that data from different technical information systems can be displayed in a single, unified record. Further, EHRs can be transferred electronically, thus reducing delays and errors in recording prescriptions or communicating laboratory test results.

The benefits of digitizing health records are substantial. Health care providers with EHR systems have reported better outcomes, fewer complications, lower costs, and fewer malpractice claim payments. But despite EHRs' potential in drastically improving the quality of medical care, only a low percentage of health care providers use EHR systems. While the advantages of EHRs are significant, they also carry concerns, including high costs, lost productivity during EHR implementation or computer downtime, and lack of EHR usability.

The Health Insurance Portability and Accountability Act (HIPAA), enacted in the U.S. in 1996, and as amended, established rules for use and access of protected health information (PHI). HIPAA provides restrictions on disclosure of and access to protected health information to and by third parties. HIPAA applies to information in electronic medical records, such as health information doctors and nurses input, documented conversations between a doctor and a patient, and information use to process or facilitate medical billing claims and documents. The HIPAA Security Rule, effective on Apr. 20, 2005 for most covered entities, adds additional constraints to electronic data security and the storage and transmission of PHI.

The high cost of EHRs also significantly hinders EHR adoption. A large number of physicians without EHRs have referred to initial capital costs as a barrier to adopting EHR systems. Cost concerns are even more severe in smaller health care settings, because current EHR systems are more likely to provide cost savings for large integrated institutions than for small physician offices. During the EHR technology's setup and implementation process, productivity loss can further offset efficiency gains. The need to increase the size of information technology staff to maintain the system adds even more costs to EHR usages.

Usability is another major factor that holds back adoption of EHRs. It is particularly challenging to develop user-friendly EHR systems. There is a wide range of data that needs to be integrated and connected. Complex information and analysis needs vary from setting to setting, among health care provider groups, and from function to function within a health care provider group. To some providers, using electronic medical records can be tedious and time consuming, and the complexity of some EHR systems renders the EHR usage less helpful. Some doctors and nurses also complain about the difficulty and the length of time to enter patients' health information into the system.

Under-utilization of EHR systems, despite incentives and mandates from the government and the tremendous potential of EHRs in revolutionizing the health care system, calls for better EHR systems that are secure, cost-effective, efficient, and user-friendly.

Comprehensive EHR systems can provide capabilities far beyond simply storing patients' medical records. Because EHR systems offer health care providers and their workforce members the ability to securely store and utilize structured health information, EHR systems can have a profound impact on the quality of the health care system. In Framework for Strategic Action on Health Information Technology, published on Jul. 21, 2004, the Department of Health & Human Services (HHS) outlined many purposes for EHR services. The outlined purposes include, among other things, improving health care outcomes and reducing costs, reducing recordkeeping and duplication burdens, improving resource utilization, care coordination, active quality and health status monitoring, reducing treatment variability, and promoting patients' engagement in and ownership over their own health care.

Recent legislation has set goals and committed significant resources for health information technology (IT). One of the many initiatives of the American Recovery and Reinvestment Act of 2009 (ARRA) was "to increase economic efficiency by spurring technological advances in science and health." The Health Information Technology for Economic and Clinical Health (HITECH) Act, passed as a part of ARRA, allocated billions of dollars for health care providers to adopt and meaningfully use EHRs in their practices. HITECH also mandates the Office of the National Coordinator for Health Information Technology (ONC) to define certification criteria for "Certified EHR Technology."

EHR systems satisfying "Certified EHR Technology" criteria are capable of performing a wide range of functions, including: entry and storage, transmission and receipt of care summaries, clinical decision support, patient lists and education resources, generation of public health submission data, and patient engagement tools. Entry and storage is related to the ability to enter, access and modify patient demographic information, vital signs, smoking status, medications, clinical and radiology laboratory orders and results. Transmission and receipt of care summaries involve the ability to receive, incorporate, display and transmit transition of care/referral summaries. Clinical decision support features configurable clinical decision support tools, including evidence-based support interventions, linked referential clinical decision support, and drug-drug and drug-allergy interaction checks. Patient lists and education resources include the ability to create patient lists based on problems, medications, medication allergies, demographics and laboratory test result values, and the ability to identify patient-specific education resources based on such data elements. Generating public health submission data allows users to create electronic immunization and syndromic surveillance data files that can be submitted to public health agencies. Patient engagement tools allow medical professionals to grant patients with an online means to view, download and transmit their health information to a third party, provide patients with clinical summaries after office visits, and facilitate secure-doctor patient messaging.

Patient and Physician Devices

Devices exist that observe aspects of a patient's health. For example, a blood glucose monitor available from Agamatrix Inc. of Salem, N.H. collects blood glucose readings using a smartphone application. In addition, devices exist that improve a doctor's productivity. For example, healthcare speech recognition solutions available from Nuance Inc. of Burlington, Mass. enable a doctor to dictate healthcare information.

These devices do not directly integrate with current EHR systems. For the data produced by these systems to be entered into an EHR, it often must be manually retyped into the patient record within the EHR. Or, in some cases the collected data may be sent to a doctor's practice as a fax, which must be converted to a PDF and imported into the patient's record.

BRIEF SUMMARY

Embodiments increase the efficiency and usability of applications that interface with EHR systems. Increasing efficiency and usability greatly encourages healthcare providers to adopt the use of EHR systems, which is advantageous for both the providers and patients.

In an embodiment, a computer-implemented method streamlines the interface between an application and an electronic health record (EHR) system. In the method, a context application program interface (API) call, made by the application being operated in real-time by a member of a medical practice, is received. In response to the context API call, the method further determines a plurality of possible contexts indicating the medical practice in the EHR system. Then, the method returns, in real-time, the plurality of possible contexts as a plurality of corresponding keys, where a key from the plurality of corresponding keys identifies an element in the EHR system.

Method and computer program product embodiments are also disclosed.

Further embodiments, features, and advantages of the invention, as well as the structure and operation of the various embodiments, are described in detail below with reference to accompanying drawings.

BRIEF DESCRIPTION OF THE DRAWINGS

The accompanying drawings, which are incorporated herein and form part of the specification, illustrate the present disclosure and, together with the description, further serve to explain the principles of the disclosure and to enable a person skilled in the relevant art to make and use the disclosure.

FIG. 7 is an illustration of a conventional medical record.

The drawing in which an element first appears is typically indicated by the leftmost digit or digits in the corresponding reference number. In the drawings, like reference numbers may indicate identical or functionally similar elements.

DETAILED DESCRIPTION

Embodiments relate to helping integrate an EHR system with a medical practice's client-side application to collect patient data. To help the integration, embodiments provide the medical practice's application information about the current context under which a medical practitioner in a medical practice is operating. For example, as will be described in greater detail below, embodiments may provide the client application information indicating the patient a physician is currently scheduled to see. In another example, embodiments may provide the client application information about pages or fields in the EHR system that members of the practice are currently accessing. Using this information, the client application can seamlessly enter new data into the current record of the EHR system.

In the detailed description that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Context API

Figure 1:
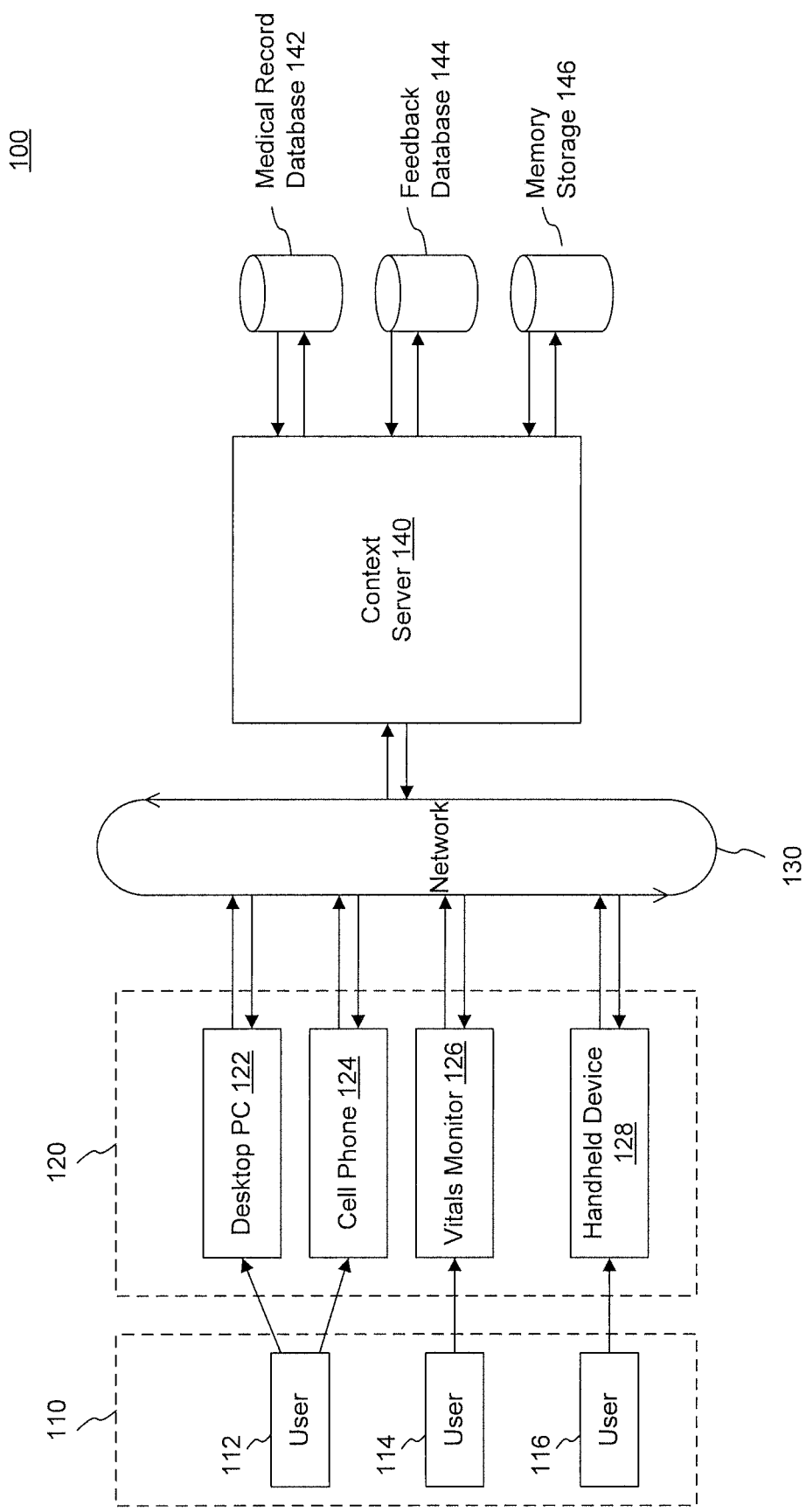
FIG. 1 is a diagram illustrating a system that helps interface an application running on a data collection device and a context server.

FIG. 1 is a diagram illustrating a system 100 that helps interface an application running on a data collection device with a context server. System 100 includes a context server 140 that communicates over one or more networks 130, such as the Internet, with a variety of devices 120 operated by various users 110. In an embodiment, medical record database 142 and context server 140 are included in an EHR system.

Context server 140 interacts with a medical record database 142. Medical record database 142 stores a history describing the health and treatment of various patients. Some of the stored data may be only accessible to the patient. Other data stored in medical record database 142 may be accessible to both the physician and patient. Still other data may be accessible only to the physician. Medical record database 142 may, for example, store patient encounters, lab results, prescriptions, messages, and records of observational data. Medical record database 142 might even store a patient's appointment scheduling information. Any of the aforementioned data may also be stored in the context of a chart note within the medical record database 142. In addition, medical record database 142 can include biographical information about a patient, such as name, address, date of birth, and information about a physician's practice, such as specialty and number of employees. The medical record database 142 comprises a component of an EHR system.

Third-party developers may develop applications that would benefit from interacting with medical record database 142. In an example, a third-party developer may want its application to be able to download patient biographical information, patient records, or practice information and automatically customize operation, without having the patient or physician manually reenter the information. In another example, an application may submit and save collected data to the patient's records in medical record database 142, to the physician's records, or to both. To enable these applications, running on devices 120, to interact efficiently in a user-friendly manner with medical record database 142, the context server 140 offers context APIs. Upon receipt of context API calls, the context server 140 return possible desired contexts to the requesting applications.

The context server 140 interacts with a feedback database 144 to determine the most likely possible contexts the user operating the application desires. Feedback database 144 can store a history of user selected contexts and associated contexts. These associated current contexts may be the operational status of the user and other users in the medical practice at the time the context API was called. In one embodiment, this information may be stored in a table where the key is a current context element and the record contains the user selected context. The record may also contain a plurality of user selected contexts associated with the current context element. In another embodiment, current context information regarding the current operational status of users 110 in the network 130 may also be stored in feedback database 144. Given the temporary nature of current context information, it may be more efficient to store this information in a separate memory storage 146. This memory storage 146 may also be incorporated within context server 140. The context server 140 uses query information from both the feedback database 144 and memory storage 146 in its adaptive algorithm to determine possible desired contexts, which it returns to the calling application.

The various applications may also communicate with the medical record database 142 through the context server 140 via network 130. The applications may run on a variety of devices 120, including a desktop personal computer (PC) 122, a cell phone 124, a vitals monitor 126, or another handheld device 128. Other devices may include other forms of health monitoring devices including vision testing equipment, MRIs, and X-ray machines. Devices may even include third-party servers and computing platforms interfacing with the context server, which has direct access to medical record database 142.

FIG. 1 shows four devices: desktop PC 122 and cell phone 124 operated by user 112, vitals monitor 126 operated by user 114, and handheld device 128 operated by user 116. A device may be operated by one more users and likewise, a user may operate one or more devices, as shown by user 112 in system 100. Users 110 are members of a medical practice and may be patients or physicians. They could also be caretakers, or other medical professionals such as office staff, nurses, or healthcare administrators. Users 110 may download third-party client applications that run on devices 120, and interact with the medical record database 142 through the context server 140.

As mentioned above, the client applications on devices 120 may communicate over network 130 to submit data to the context server 140. Network 130 may be, for example, a wide area network, such as the Internet. In some embodiments, the client applications may also interact with devices local to the user.

In one embodiment, user 114 may be a nurse who has monitored a patient's health condition via vitals monitor 126. User 116 may be a medical receptionist who is scheduling appointments on a handheld device 128 like an iPad. User 112 may be a doctor currently examining the patient. The doctor may simultaneously be opening a patient's record through an EHR application on a desktop PC 122. The doctor may also be running a third-party medical transcription application on his cell phone 124 or smart phone. With this application, he can transcribe the patient's symptoms, his examination, and his prescriptions without pausing to insert the said information manually. After completing transcription, he would want to save the information to the medical record database 142. The transcription application would call a context API. Upon receipt of the call, the context server 140 would determine possible desired contexts given the current context and return the possible desired contexts. In this embodiment, the context server would return a patient, the patient's current chart note, and possibly multiple chart notes if they have been accessed during previous sessions. Upon the doctor's verification of the desired context, the data would be saved to the patient's record or the specific chart note in the medical record database 142. In this way, by identifying the context of the medical practice including the context of the medical practitioner within an EHR system, context server 140 helps integrate devices 122-128 with the EHR system.

Figure 2:
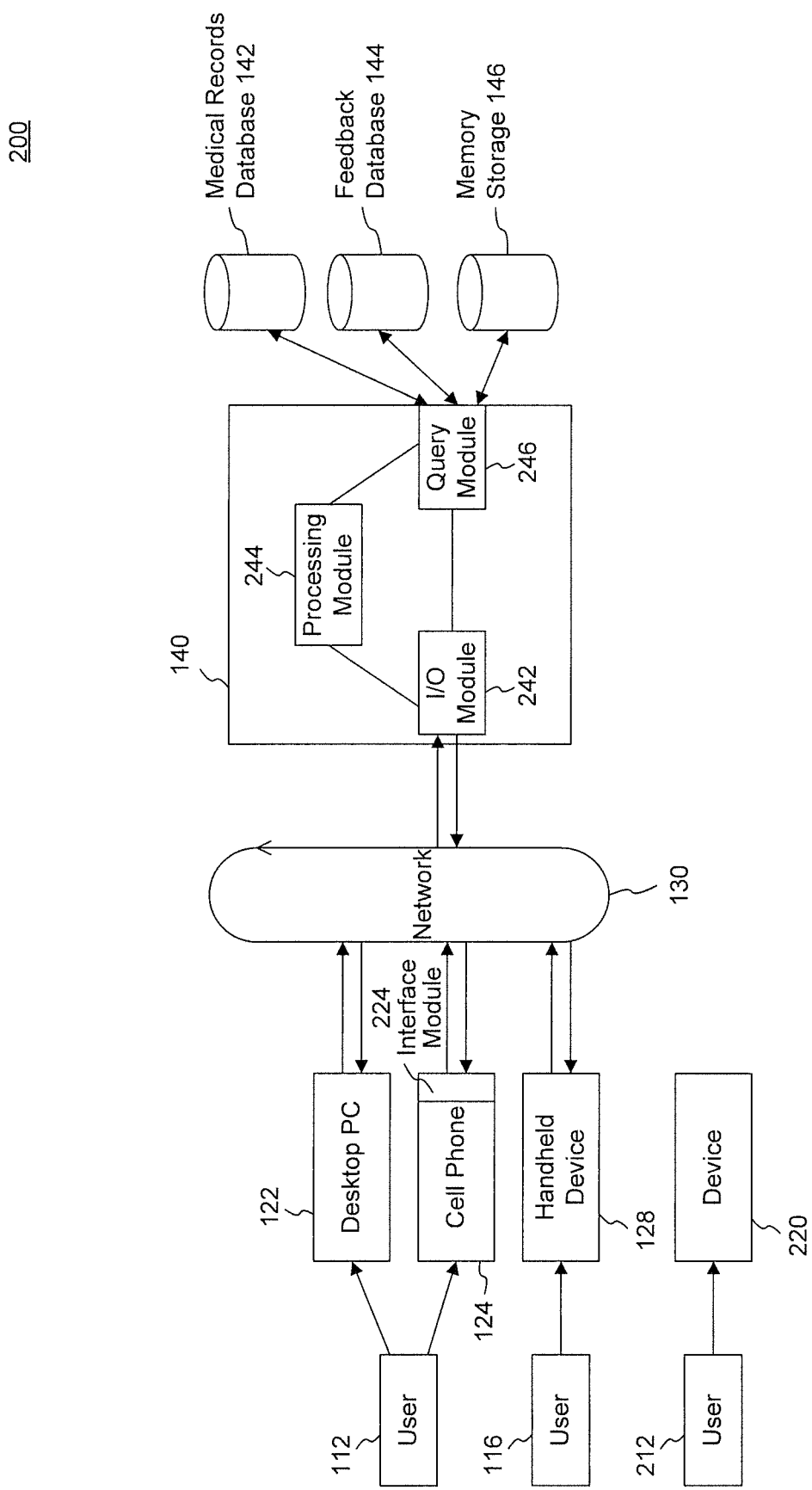
FIG. 2 is a diagram illustrating the system of FIG. 1 in greater detail.

To provide the context to third party integrations, context server 140 includes various modules as illustrated in FIG. 2. FIG. 2 is a diagram illustrating a system 200 that includes the context server 140, devices, and databases of FIG. 1, Included in the context server and cell phone 124, system 200 illustrates modules. In particular, context server 140 includes an Input/Output module (I/O module 242), a processing module 244, and a query module 246, and cell phone 124 includes an interface module 224. System 200 also illustrates a device 220 operated by user 212 that is not in communication with network 130.

Interface module 224 is within an application running on cell phone 124 and acts as an interface between the application and the context server 140. When a doctor such as user 112 is finished transcribing the objective field of a chart note on a transcription application running on his cell phone, device 124, she may request that the data be saved to the medical records server. Interface module 224 would initiate a context API call in response to the save request and submit the call through network 130 to I/O (input/output) module 242 on the context server 140. The interface module 224 is also responsible for presenting the plurality of returned possible desired contexts determined by the context server 140, sent by I/O module 242, to the user 112 using cell phone 224. Finally, after the desired context is selected and verified, the interface module submits the selected and verified context along with data to be saved in the medical record database 142 to the context server 140.

I/O module 242 is an interface module between the devices and the context server 140. The I/O module 242 can not only receive a context API call from an application running on a device such as device 124, but also it can receive all current context information transmitted through the network 130 from all the devices operating in real-time on the network 130. In system 200, this would include devices 122, 124, and 128, but not device 220 because device 220 is not in communication with network 130. The current context information received by I/O module 242 can be stored on a separate storage such as memory storage 146 or a feedback database 144 through interactions with the query module 246. I/O module can also take the role of verifying a desired context by prompting the user to select and verify a desired context from the plurality of possible contexts returned by the context server 140 to the application running on cell phone 124. This verification role may instead be performed by the interface module 224 running on cell phone 124 instead.

In addition to receiving, I/O module 242 can also transmit the plurality of possible desired contexts determined by a processing module 244. It may transmit all of or only a subset of the possible desired contexts. It can also transmit possible desired contexts in a prioritized list, wherein contexts (and the associated key) with a higher confidence level may have higher priority.

Query module 246 is an interface module to external databases such as medical record database 142 and feedback database 144, and external memory storage 146. Query module 246 may retrieve information from the medical record database 142 or save data and the associated selected desired context from the interface module 224 received by the I/O module 242 on the context server 140 to database 142. Likewise query module 246 can retrieve current context information from the memory storage 146 to determine a plurality of possible contexts or update the current context information stored in memory storage 146 as it receives new current context information from devices (such as devices 122, 124, and 128) operating in real-time. Finally, query module 246 retrieves relevant information from feedback database 144 used in determining a confidence level associated with each of the possible contexts and updates feedback database 144. Updates comprise information disclosed in preceding embodiments, including user customization preferences regarding desired contexts and a history of selected desired contexts.

Finally, processing module 244 determines the set of possible contexts, which is determined in part by the current context information stored on memory storage 146 queried by query module 246. The processing module 244 also uses an adaptive algorithm to calculate the confidence level associated with each of the possible contexts, identified by a key. The processing module 244 may also determine a subset of the plurality of possible contexts to be submitted to the interface module 224 by I/O module 242.

Figure 3:
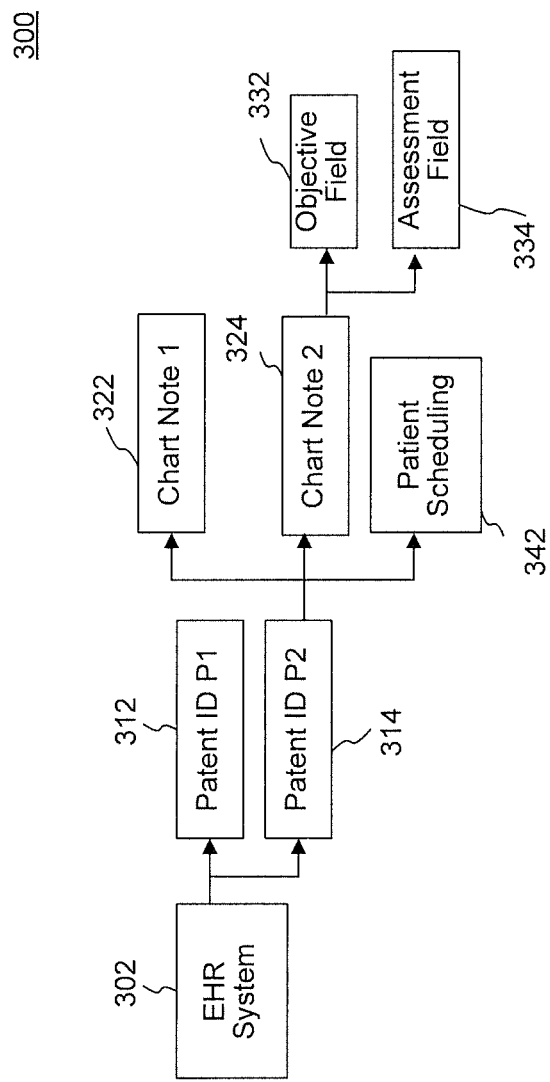
FIG. 3 is a diagram illustrating a hierarchy of current contexts.

FIG. 3 illustrates a hierarchy of possible desired contexts a user may want. At the highest level, the desired context may be a particular EHR system 302. This context may be particularly useful for healthcare administrators maintaining multiple EHR systems. A doctor seeing a patient for the first time may also desire this context to create a new patient in the EHR system 302. This context can be divided into a patient context such as patient 312 with a Patient ID P1 and a patient 314 with Patient ID P2. This may be the desired context for a doctor who wishes to save a new chart note to a recurring patient already in the EHR system.

An even finer desired context can be the chart notes or patient scheduling data associated with the patient from the medical record database 142. In the embodiment in FIG. 3, chart note 322, chart note 324, and patient schedule 342 is associated with patient 314. A medical receptionist may desire the patient scheduling data to schedule a new appointment in real-time. A nurse may desire a chart note context of a patient to save monitoring data immediately after the monitoring. Finally, a doctor may desire a patient's chart note to save examination data immediately after examination. In fact, a doctor may desire an even finer context, particularly fields such as objective field 332 or assessment field 334 of the chart note 324 that he may save data to when he needs to. It should be clear to one of ordinary skill in the art that other fields associated with the chart note, other data associated with the patient, and other information records associated with the EHR system are possible.

Figure 4:
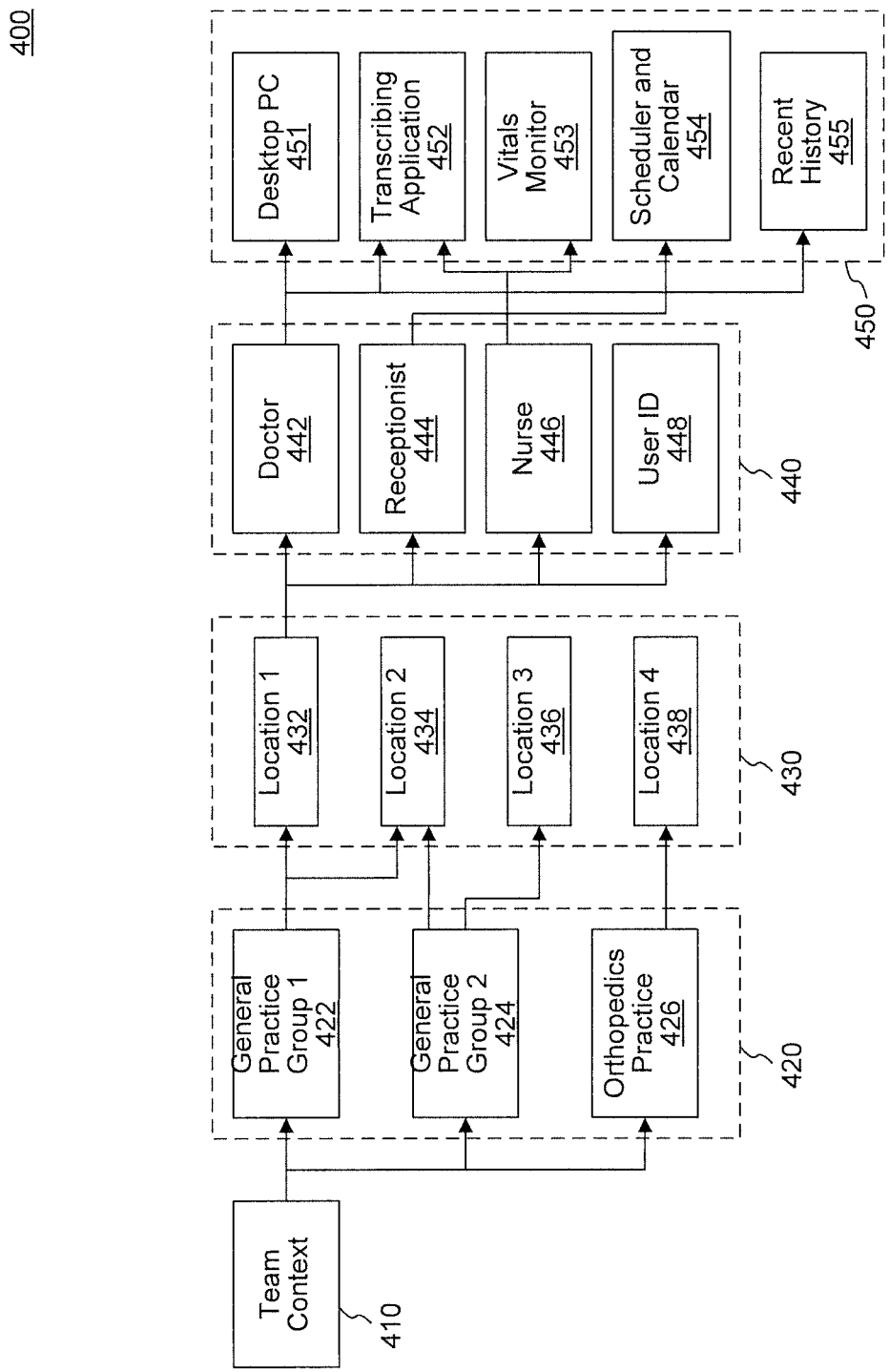
FIG. 4 is a diagram illustrating a hierarchy of returned contexts.

In an embodiment, the current context can include various information about the user. FIG. 4 illustrates a hierarchy of possible current context information elements. The broadest information is the team context 410. This may embody all the users in a medical facility, a group of facilities, an organization that many physicians belong to, or even an insurance company. Team context 410 may include multiple practices 420, such as general practice group 1 422, general practice group 2 424, or even an orthopedics practice 426 within the team context. The practice context 420 can be further divided into a location or facilities context 430 if there are multiple locations. For example, in FIG. 4, general practice 422 operates at two locations 432 and 434. In an example embodiment, the context server may use this current context data, particularly the practice and location context, to disambiguate patients with similar or identical names and provide a desired context with a higher confidence.

The location context can be further divided into the user's context 440. User's context 440 may include the user's role such as doctor 442, nurse 446, or receptionist 444. This user context may also be user identification (ID) 448. For a doctor, user ID 448 may be his National Provider Identifier (NPI). In an embodiment, context server 140 can use the user's role to determine how likely a possible context is the desired context. For example, if the user has the role of a receptionist 444, the likelihood she desires the context of patient scheduling 342 may be greater than other roles. Likewise, a doctor is more likely to desire a patient ID, a chart note, or a chart note field context. Appropriately, context server 140 can calculate a confidence level/score for a possible context, such as the patient scheduling context 442, representing the likelihood that possible context is the desired context. For a user with a receptionist role 444, the confidence score may be significantly higher than if the context requesting user is associated with a nurse 446 context.

Finally, at the finest granularity, the current context can include information about the application (application context 450) the user is operating. Various users with particular role contexts 442, 444, and 446 using variety of applications 451-454 are depicted in FIG. 4. For a user with a doctor 442 role using a transcribing application 452, context server 140 will be more confident the likely desired context is a field such as objective field 334 of a patient's chart note 1 324. The current context can not only include what type of application a member of a medical practice is currently using, such as an EHR application on desktop PC 351, but also include operations occurring within the application. For example, the current context can also include information such as a patient identification associated with the current window or browser or tab open in the foreground, the current cursor location, or where a cursor click was last made. In one embodiment, referring back to FIG. 1, for a user using the transcription application on device 124, the context server 140 can use the current context of the cursor location or last clicked location to determine which field of a chart note the user likely desires next. In another embodiment, current context can include a history of recently selected contexts (recent history 455) or contexts associated with data the user is currently viewing.

Figure 5A:
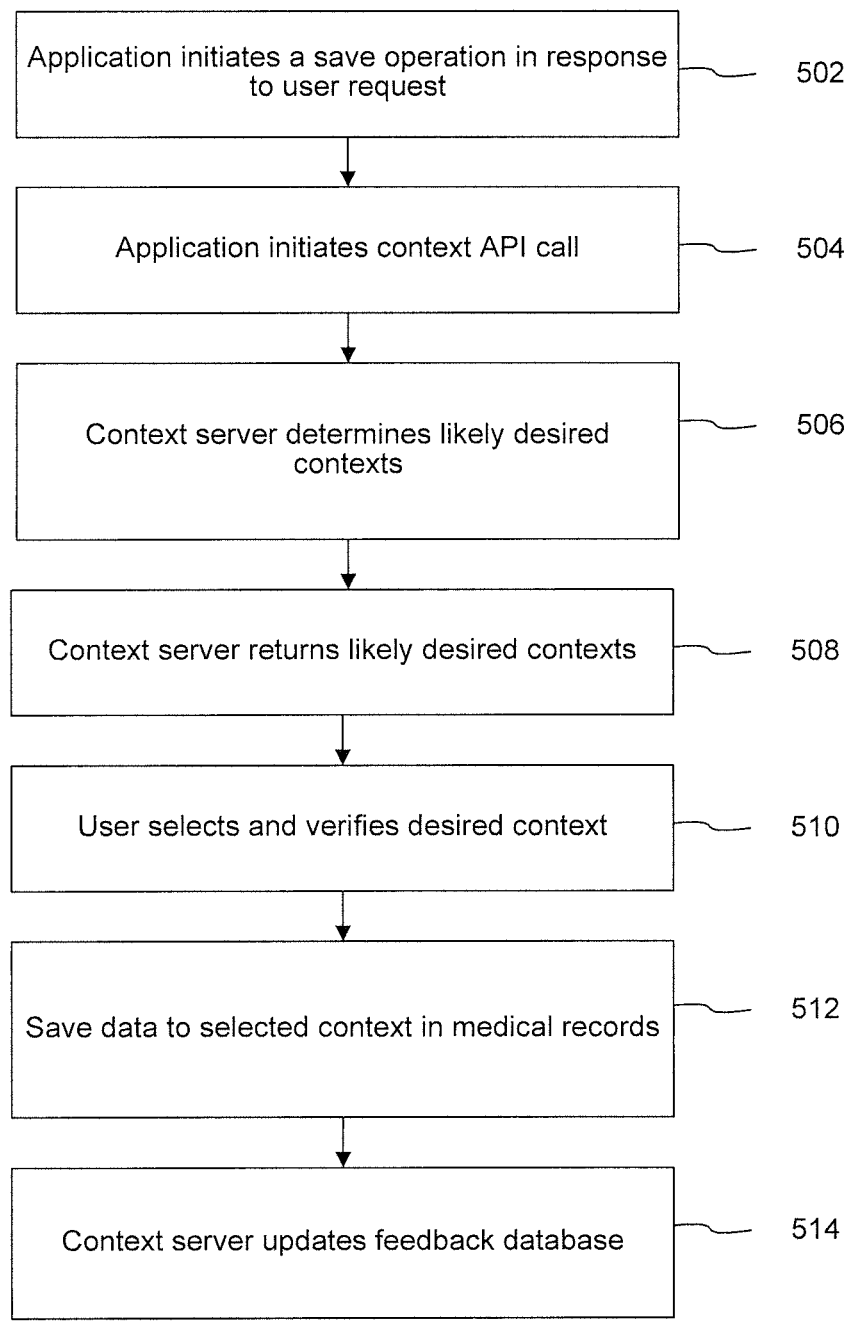
FIG. 5A-B are flowcharts illustrating example methods of helping integrate the interface between the application operated by a medical member with an EHR system.
Figure 5B:
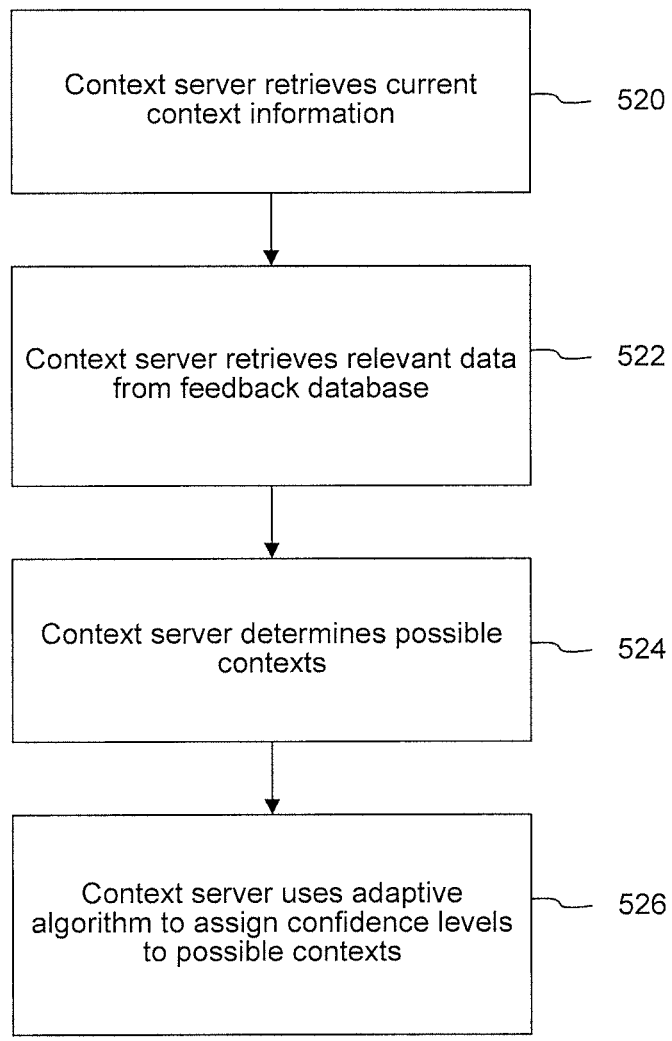

FIGS. 5A-B are flowcharts illustrating example methods of helping integrate the application operated by a medical member with an EHR system. FIG. 5A illustrates a method 500A starting at a step 502 where an application initiates a save data operation based on a user's request. In an example embodiment, user 114 is a nurse operating vitals monitor 126. After user 114 measures the patient's condition, user 114 initiates a save operation in an application running on vitals monitor device 126 to save the measured information to the patient's records in medical record database 142 of the EHR system. This initiation may be made by locating the save operation option in a menu within the application. It may be made with a few clicks of the cursor or even with customizable gestures and/or finger tap(s) on a device with a touch screen.

At step 504, in response to the application initiating a save data operation, the application makes a context API call. This context API call may be just one of many API calls provided by context server 140 that allows for a more streamlined interface between the application and medical record database 142. Current context information of user 114, one or more elements depicted in FIG. 4, may be embedded within the context API call to be sent to context server 140. This may be the role context indicating user 114 is a nurse or information indicating the calling application is running on vitals monitor 126. This embedded context can also include the nurse's user ID 448. This current context information may also be submitted in separate API calls.

After the receipt of the context API call, context server 140 determines a plurality of possible desired contexts in step 506. This determination may be based on user 114's customizations, which may be part of the submitted current context information. A customization may be the desired context is always in the form of a patient's chart note. Context server 140 may save this customization and user 114's associated user ID 448 to a table in feedback database 144. Other user 114's current context information such as the user's role as a nurse 446 can be used to further differentiate the type of desired context. A nurse likely desires a patient ID context such as patient ID P2 314 or potentially a patient's chart note 2 324.

The determination is also made in part based on the current context information of other users 110 in the medical practice. For example, the current context information of the receptionist 116 running a patient scheduling application on handheld device 128 may include information about patients scheduled around the time of the initiated context API call. The likelihood the desired context of user 114 with the role of receptionist 116 involves one of the patients scheduled at the time the measurements were taken is greater than for other roles.

At step 508, the context server returns a plurality of likely desired contexts to the application after determining likely possible contexts. In the foregoing embodiment, user 114 may see the plurality of possible desired contexts displayed in the application running on vitals monitor 126 as a set of keys. The key may be a string of alphanumeric digits representing the context. For example a key for a patient context may be "U123" or "JohnDoe23" etc. and a key for location might be "USA_NY2." The user interface may display the set of possible desired context as a list of keys. The list may be a prioritized list with more likely desired contexts (represented as keys) towards the top of the list. In another embodiment, the returned possible contexts can be displayed in the form of a tree structure which may better encapsulate the returned possible contexts since returned possible contexts can be of different granularities (see FIG. 3 which illustrates different types of returned contexts). Other user interface embodiments may be possible, easily implemented, and possibly customized.

At step 510, the user operating the application selects and verifies the desired context from the plurality of returned possible contexts. User 114 would select chart note 2 324 indicating the patient, whose vitals he has measured through vitals monitor 126. This selected desired context can be associated with recent history 455, which is an element of the current context, and used as a key in subsequent API calls and other read and write API calls. The verification ensures the collected data is saved to the correct patient's records. For example, context server 140 may differentiate patients with the same names in medical record database 142 of the EHR system based on the current context information context server 140 has received. A user verification step ensures the differentiation was made correctly. In an embodiment if the desired context was not one of the returned contexts, user 114 may need to submit the desired context manually. The user interface for the selection and verification may be any that a person skilled in the technical arts would implement.

In step 512, the application would save the collected data to the selected and verified desired context. In the foregoing embodiment, the application running on device 128 would send vitals data through network 130 to context server 140. Context server 140 would save this data to the desired context in medical record database 142 of the EHR system.

Finally in step 514, context server 140 may update feedback database 144. The updated records may include those indicating the user's customizations. Context server 140 may add and/or update current contexts and the associated user selected desired context to feedback database 144. Step 514 need not be executed after completing the save operation. It can be executed concurrently for example with step 512 or after the user selection and verification of desired context in step 510.

FIG. 5B illustrates a method 500B detailing other operations involved in the possible desired contexts determination step 506 of method 500A. In this embodiment, as part of the determination step 506, context server 140 first retrieves current context information from memory storage 146 in step 520. Current context information of all the users 110 operating devices 120 may be continually sent from devices 120 through network 130 to context server 140. Context server 140 may continually update the current context information in memory storage 146 such that the information stored in memory storage 146 reflect the operational statuses of all the users operating devices in real time. Context server 140 may retrieve only the current context of the user initiating the context API call, the current contexts of all the users at a medical facility, the current contexts of all the users in the practice, or any other subset of all the current contexts recorded in memory storage 146.

At step 522, context server 140 retrieves relevant data from the feedback database 144. Context server 140 may look up customization preferences recorded in feedback database 144 by using the retrieved current context information, such as user 114's user ID 448, as a key into a customizations table in feedback database 144. Context server 140 may also query feedback database 144 for past selected desired contexts associated with some subset of the current context information retrieved in step 520. In an embodiment, context server retrieves both behavioral data (e.g. history of selected context and associated current contexts) as well as explicit data (e.g. user customizations) from feedback database 144.

At step 524, context server 140 determines a set of possible desired contexts. This determination is made based on the current contexts retrieved in step 520 and possibly data retrieved in step 522. For example, if the operating user is a particular doctor, this set of possible desired contexts may include all of the doctor's patients, such as patient ID P2 314 representing the patient. This data, patients associated with a user, may be saved as part of a user's customization options or in a separate database in the EHR system. This set of possible desired contexts may also include all of the contexts associated with patients scheduled for the day, retrieved from the current context information of a scheduling application.

Finally in step 526, context server 140 uses an adaptive algorithm to assign confidence levels to the determined possible contexts. These confidence levels indicate how likely a possible context of the set of possible contexts will ultimately be the desired context selected and verified by a user. The adaptive algorithm may be a variation of any of the machine learning algorithms that are known in the prior art today. Factors used by the algorithm include both user customization information and behavioral information retrieved in step 522. The confidence levels, associated possible contexts, and user selected desired context information may be saved in feedback database 144. The adaptive algorithm uses past accuracy statistics to adjust parameters that will more accurately assign confidence levels to possible contexts.

In addition to step 508, the context server may return only a subset of the determined possible contexts based on some requirement. For example, perhaps only possible contexts with a confidence score, determined in step 526, above a certain threshold are returned or only a proportion of possible contexts are returned. The number of returned possible contexts may even be limited based on a user allotted time to complete the context API call.

Example Computing Device

Each of the servers and modules in FIGS. 1 and 2 may be implemented on the same or different computing devices in hardware, software, or any combination thereof. Such computing devices can include, but are not limited to, a personal computer, a mobile device such as a mobile phone, workstation, embedded system, game console, television, set-top box, or any other computing device. Further, a computing device can include, but is not limited to, a device having a processor and memory, including nontransitory memory, for executing and storing instructions. The memory may tangibly embody the data and program instructions. Software may include one or more applications and an operating system. Hardware can include, but is not limited to, a processor, memory, and graphical user interface display. The computing device may also have multiple processors and multiple shared or separate memory components. For example, the computing device may be a part of or the entirety of a clustered computing environment or server farm.

Figure 6:
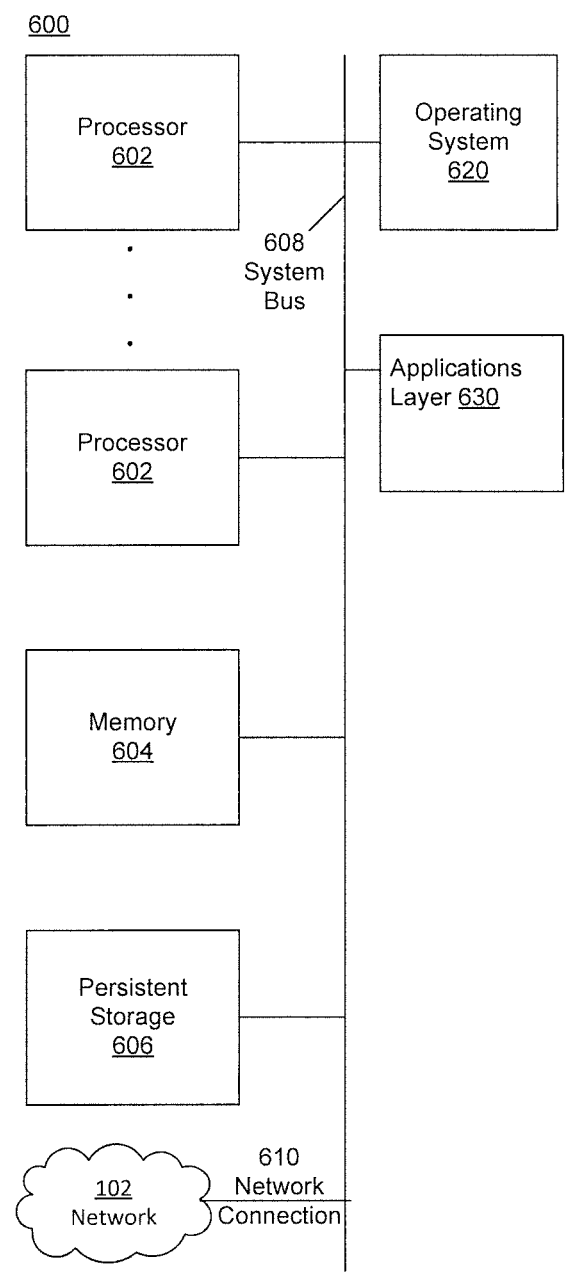
FIG. 6 is a diagram illustrating an example computing device, according to an embodiment.

An example computing device is illustrated in FIG. 6. FIG. 6 is a diagram illustrating a computing device 600 that accesses a network 102 over a network connection 610 that provides computing device 600 with telecommunications capabilities. Computing device 600 uses an operating system 620 as software that manages hardware resources and coordinates the interface between hardware and software.

In an embodiment, computing device 600 contains a combination of hardware, software, and firmware constituent parts that allow it to run an applications layer 630. Computing device 600, in embodiments, may be organized around a system bus 608, but any type of infrastructure that allows the hardware infrastructure elements of computing device 600 to communicate with and interact with each other may also be used.

Processing tasks in the embodiment of FIG. 6 are carried out by one or more processors 602. However, it should be noted that various types of processing technology may be used here, including multi-core processors, multiple processors, or distributed processors. Additional specialized processing resources such as graphics, multimedia, or mathematical processing capabilities may also be used to aid in certain processing tasks. These processing resources may be hardware, software, or an appropriate combination thereof. For example, one or more of processors 602 may be a graphics-processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

To manipulate data in accordance with embodiments describe herein, processors 602 access a memory 604 via system bus 608. Memory 604 is nontransitory memory, such as random access memory (RAM). Memory 604 may include one or more levels of cache. Memory 604 has stored therein control logic (i.e., computer software) and/or data. For data that needs to be stored more permanently, processors 602 access persistent storage 606 via system bus 608. Persistent storage 606 may include, for example, a hard disk drive and/or a removable storage device or drive. A removable storage drive may be an optical storage device, a compact disc drive, flash memory, a floppy disk drive, a magnetic tape drive, tape backup device, and/or any other storage device/drive.

Processors 602, memory 604, and persistent storage 606 cooperate with operating system 620 to provide basic functionality for computing device 600. Operating system 620 provides support functionality for applications layer 630.

Network connection 610 enables computer device 600 to communicate and interact with any combination of remote devices, remote networks, remote entities, etc. For example, network connection 610 may allow computer device 600 to communicate with remote devices over network 102, which may be a wired and/or wireless network, and which may include any combination of LANs, WANs, the Internet, etc. Control logic and/or data may be transmitted to and from computer device 600 via network connection 610.

Applications layer 630 may house various modules and components. For example, the applications and modules in FIGS. 1, 2, and 4 may be included in applications layer 630.

It should be noted that computer-readable medium embodiments may include any physical medium which is capable of encoding instructions that may subsequently be used by a processor to implement methods described herein. Example physical media may include floppy discs, optical discs (e.g. CDs, mini-CDs, DVDs, HD-DVD, Blu-ray), hard drives, punch cards, tape drives, flash memory, or memory chips. However, any other type of tangible, persistent storage that can serve in the role of providing instructions to a processor may be used to store the instructions in these embodiments.

Comprehensive EHR System

A comprehensive EHR system includes a variety of components. Components of EHR systems vary from vendor to vendor and from setting to setting. For example, an EHR system in which embodiments of the present invention can be used may also include: (1) an electronic prescription (eRx) component, (2) a clinical and radiology laboratory component, (3) a transfer of care component, (4) a scheduling component, (5) a billing service component, and (6) a patient portal component.

The electronic prescription component provides medical professionals capabilities to electronically generate and transmit prescriptions for patients' medications. Some EHR systems enable prescribers to view their patients' prescription benefit information at the point of care and select medications that are on formulary and covered by the patient's drug benefit. This informs physicians of potential lower cost alternatives (such as generic drugs) and reduces administrative burden of pharmacy staff and physicians related to benefit coverage.

The clinical and radiology laboratory component allows medical professionals to integrate with clinical laboratories to electronically receive and incorporate clinical laboratory tests and results into a patient's chart and create computerized provider order entry ("CPOE") clinical laboratory orders. This component can also support functionality that enables medical professionals to electronically receive and incorporate radiology laboratory test results (e.g., x-ray, ultrasound, MRI, PET/CT scan, mammography) into a patient's chart.

Medical professionals can use the transfer of care component to transmit referrals electronically to other EHR users or to non-users by facsimile. Additionally, some EHR systems support electronically creating and transmitting consolidated continuity of care documents.

The scheduling component offers functionality that allows healthcare providers to manage their appointments with an electronic schedule that can be integrated into a practice's workflow.

The billing service component offers medical professionals the ability to electronically generate and transmit superbills. Superbills are the data source for the creation of a healthcare claim. The billing service component can transmit superbills to medical billing software accounts controlled by the professionals' offices or their billing service providers. This component also allows a healthcare professional to save a superbill and transmit it to the health care professional's billing account with the billing software vendor.

The patient portal component allows medical professionals to grant their patients an online means to view, download, and transmit their health information, often called the personal health record (PHR). This component also provides patients with the ability to review their physicians and send and receive secure messages directly to and from their physicians.

Together, these components leverage the benefits of EHRs while mitigating the risks.

CONCLUSION

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computer-implemented method to help an application operate more efficiently on data elements of an electronic health record (EHR) system, comprising:
    receiving, from the application operated by a member of a medical practice interacting with a patient, a context application program interface (API) call; and
    in response to the context API call:
        retrieving a current status of the member in the application with respect to the patient,
        determining, based on the current status, a plurality of keys, each key identifying one possible EHR element that is related to information of the patient in the EHR system,
        for each key, calculating, by an adaptive algorithm based on historical activity of the member within a status similar to the current status of the application, a confidence value indicating how likely that key is to be selected by the member,
        selecting, by the adaptive algorithm from the determined plurality of keys, a key that identifies a possible EHR element, the key selected based on whether the calculated confidence value for the selected key is above a threshold value, and returning the selected key to the application, wherein responsive to receiving the selected key, the application prompts the member to verify that the selected key corresponds to a correct EHR element such that after the verification, the application uses the selected key to operate on the correct EHR element in the EHR system.

2. The method of claim 1, further comprising:

retrieving a second current status of a second member in a second application with respect to the patient, wherein the second member is from the medical practice, and wherein the calculation is based on the current status and the second current status.

3. The method of claim 1, wherein the context API call is initiated in response to a save request by the application to save a set of data, wherein the selected key is a first key, the method further comprising:

in response to the context API call:

selecting, from the determined plurality of keys, a second key that identifies a possible EHR element, the second key selected based on whether the calculated confidence value for the second selected key is above the threshold value, and returning the selected first and second keys to the application, wherein responsive to receiving the selected first and second keys, the application prompts the member to verify one of the selected first and second keys as a key that corresponds to the correct EHR element such that after the verification, the application uses the verified key to save the set of data to the possible EHR element identified by the verified key.

4. The method of claim 3, wherein the verified key is used in subsequent read or write API calls.

5. The method of claim 1, wherein the possible EHR element is a selected one of a patient, a patient's chart note, and a field of the patient's chart note.

6. The method of claim 1, wherein the current status is a selected one of a role of the member, a current cursor position in the application, a last accessed field in the application, and a current task of the application in the foreground.

7. The method of claim 1, wherein the calculation is performed based on a history of past selected keys, further comprising:

saving the current status, the plurality of keys, and the history of past selected keys in a feedback database; and using, by the adaptive algorithm, data from the feedback database in a subsequent calculation.

8. The method of claim 3, wherein the first and second keys are returned in an order based on the respective calculated confidence values.

9. A computer-implemented system to help an application operate more efficiently on data elements of an electronic health record (EHR) system, comprising:

a computing device;

a medical record database;

a context application program interface (API) server, implemented on the computing device, that receives from the application operated by a member of a medical practice interacting with a patient, a context API call; and a processing module on the context API server that in response to the context API call, retrieves a current status of the member in the application with respect to the patient, determines, based on the current status, a plurality of keys, each key identifying one possible EHR element that is related to information of the patient in the EHR system, for each key, calculates, by an adaptive algorithm based on historical activity of the member within a status similar to the current status of the application, a confidence value indicating how likely that key is to be selected by the member, selects, by the adaptive algorithm, from the determined plurality of keys, a key that identifies a possible EHR element, the key selected based on whether the calculated confidence value for the selected key is above a threshold value, and returns the selected key to the application, wherein responsive to receiving the selected key, the application prompts the member to verify that the selected key corresponds to a correct EHR element such that after the verification, the application uses the selected key to operate on the correct EHR element in the EHR system.

10. The system of claim 9, wherein the processing module retrieves a second current status of a second member in a second application with respect to the patient, wherein the second member is from the medical practice, and wherein the calculation is based on the current status and the second current status.

11. The system of claim 9, further comprising:

a feedback database;

a memory storage;

an interface module on the context API server, that in response to receiving the context API call initiated by a save request, from the application, to save a set of data, saves the retrieved current status to the memory storage; and an I/O module, that in response to returning the selected key causing the application to use the selected key to operate on the EHR element:

receives the selected key verified by the member, the verified key corresponding to the correct EHR element;

saves the selected key to the feedback database; and saves the set of data to the possible EHR element in the medical record database.

12. The system of claim 11, wherein the determination is based on looking up data from the feedback database.

13. The system of claim 12, wherein the adaptive algorithm uses data from at least one of the feedback database and the memory storage to perform the calculation.

14. A program storage device tangibly embodying a program of instructions executable by at least one machine to perform a method to help an application operate more efficiently on data elements of an electronic health record (EHR) system, comprising:

receiving, from the application operated by a member of a medical practice interacting with a patient, a context application program interface (API) call; and in response to the context API call:

retrieving a current status of the member in the application with respect to the patient, determining, based on the current status, a plurality of keys, each key identifying one possible EHR element that is related to information of the patient in the EHR system, for each key, calculating, by an adaptive algorithm based on historical activity of the member within a status similar to the current status of the application, a confidence value indicating how likely that key is to be selected by the member, selecting, by the adaptive algorithm from the determined plurality of keys, a key that identifies a possible EHR element, the key selected based on whether the calculated confidence value for the selected key is above a threshold value, and returning the selected key to the application, wherein responsive to receiving the selected key, the application prompts the member to verify that the selected key corresponds to a correct EHR element such that after the verification, the application uses the selected key to operate on the correct EHR element in the EHR system.

15. The program storage device of claim 14, wherein the context API call is initiated in response to a save request by the application to save a set of data, wherein the selected key is a first key, the method further comprising:

in response to the context API call:

selecting, from the determined plurality of keys, a second key that identifies a possible EHR element, the second key selected based on whether the calculated confidence value for the second selected key is above the threshold, and returning the selected first and second keys to the application, wherein responsive to receiving the selected first and second keys, the application prompts the member to verify one of the selected first and second keys as a key that corresponds to the correct EHR element such that after the verification, the application uses the verified key to save the set of data to the possible EHR element identified by the verified key.

16. The program storage device of claim 14, wherein the calculation is performed based on a history of past selected keys, further comprising:

saving the current status, the plurality of keys, and the history of past selected keys in a feedback database; and using, by the adaptive algorithm, data from the feedback database in a subsequent calculation.

* * * * *